United States Patent [19]
Cullen

[11] Patent Number: 6,118,022
[45] Date of Patent: Sep. 12, 2000

[54] SYNTHESIS OF PHOSPHONOMETHYLIMINODIACETIC ACID WITH REDUCED EFFLUENT

[75] Inventor: Barry A. Cullen, Lyndeborough, N.H.

[73] Assignee: Hampshire Chemical Corp., Lexington, Mass.

[21] Appl. No.: 09/388,409

[22] Filed: Sep. 1, 1999

Related U.S. Application Data

[60] Provisional application No. 60/099,490, Sep. 8, 1998.

[51] Int. Cl.$^7$ ........................................................ C07F 9/38
[52] U.S. Cl. ................................................ 562/17; 562/16
[58] Field of Search ...................................... 562/11, 16, 17

[56] References Cited

U.S. PATENT DOCUMENTS

| | | | |
|---|---|---|---|
| 2,895,989 | 7/1959 | Sexton et al. | 260/534 |
| 3,808,269 | 4/1974 | Bragdon et al. | 260/534 |
| 3,950,402 | 4/1976 | Franz | 260/502.5 |
| 3,954,848 | 5/1976 | Franz | 562/17 |
| 3,969,398 | 7/1976 | Hershman | 260/502.5 |
| 4,002,672 | 1/1977 | Smith | 260/502.5 |
| 4,147,719 | 4/1979 | Franz | 260/501.12 |
| 4,579,689 | 4/1986 | Hershman et al. | 260/502.5 |
| 4,582,650 | 4/1986 | Felthouse | 260/502.5 |
| 4,696,772 | 9/1987 | Chou | 260/502.5 |
| 4,724,103 | 2/1988 | Gentilcore | 260/502.5 |
| 4,775,498 | 10/1988 | Gentilcore | 562/17 |
| 4,898,972 | 2/1990 | Fields, Jr. et al. | 562/17 |
| 4,931,585 | 6/1990 | Pelyva et al. | 562/17 |
| 5,095,140 | 3/1992 | Fields, Jr. | 562/17 |
| 5,179,228 | 1/1993 | Martin Ramon et al. | 562/17 |
| 5,312,973 | 5/1994 | Donadello | 562/17 |
| 5,527,953 | 6/1996 | Jones et al. | 562/17 |
| 5,688,994 | 11/1997 | Baysdon et al. | 562/17 |

FOREIGN PATENT DOCUMENTS

96/38455 12/1996 WIPO.

*Primary Examiner*—Jean F. Vollano
*Attorney, Agent, or Firm*—Craig E. Mixan

[57] ABSTRACT

A process for the preparation of phosphonomethylglycine in high yields is disclosed. In accordance with the process of the present invention, alkali metal IDA, such as disodium IDA, is reacted with a strong mineral acid, such as HCl, to convert the salt of IDA to IDA. The IDA is then converted to soluble IDA phosphite salt by the addition of phosphorous acid, and the alkali metal salt of the strong acid is precipitated. The phosphite salt of IDA is phosphonomethylated, such as by the addition of $PCl_3$ and formaldehyde. Optionally, phosphorous trichloride can be hydrolyzed to provide the phosphorous acid source for phosphonomethylation of the phosphite salt.

9 Claims, No Drawings

SYNTHESIS OF PHOSPHONOMETHYLIMINODIACETIC ACID WITH REDUCED EFFLUENT

RELATED U.S. APPLICATION DATA

This application claims priority to provisional application No. 60/099,490 filed Sep. 8, 1998.

BACKGROUND OF THE INVENTION

The present invention relates to N-phosphonomethyliminodiacetic acid ("PMIDA") of the formula (I):

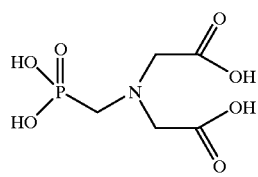

(I)

and to N-phosphonomethylglycine. Compound I is an important intermediate in the formation of N-phosphonomethylglycine ("glyphosate"), which is a translocated, postemergence, broad spectrum herbicide.

One conventional processes for the preparation of PMIDA starts with iminodiacetic acid (IDA), and requires the involved preparation of that material from its alkali metal salt. More specifically, the IDA moiety is produced by the alkaline hydrolysis of iminodiacetonitrile (IDAN) or by the oxidative dehydrogenation of diethanolamine under alkaline conditions. If sodium hydroxide is used as the base, the product from either of these methods is an aqueous disodium iminodiacetate (DSIDA) solution. This solution is the feedstock used either directly for conversion to PMIDA or to produce IDA for subsequent conversion to PMIDA. In the second case, disodium IDA solution is typically acidified with sulfuric acid or other strong mineral acid and the resulting IDA is separated from sodium sulfate or sodium salt of the strong mineral acid by fractional crystallization. This isolation of IDA by fractional crystallization, which is described in U.S. Pat. No. 3,808,269, requires an evaporative crystallizer for crystallization of anhydrous sodium sulfate, a cooling crystallizer for crystallization of IDA, two centrifuges, solids conveying equipment, and a sodium sulfate dryer, and storage silos or bins for the isolated IDA and dry sodium sulfate. Mother liquors can be recycled but a portion must be purged to remove impurities. An economically and environmentally significant amount of IDA is lost in this purge stream.

Alternatively, IDA can be isolated by ion exchange, as described in U.S. Pat. No. 2,895,989. Dilute hot disodium IDA solution is passed through a column containing a strongly acidic ion exchange resin at a temperature sufficient to prevent crystallization of the IDA acid which is formed in the column. During the ion exchange reactions, hydrogen ion from the resin is exchanged for sodium ion from the disodium IDA. Maximum recovery of IDA occurs when the equivalents of sodium ion in the disodium IDA feed exactly equals the capacity of the resin. The products are a hot solution of IDA acid and exhausted ion exchange resin in the sodium form. A waste stream of dilute sodium chloride is produced which contains only a trace of IDA. The recovery of IDA acid from disodium IDA is >99%. The IDA acid solution, however, is dilute and must be evaporated to produce a concentration useful for conversion to PMIDA. Such a concentration, however, is far above the solubility limit of IDA acid; therefore, IDA acid must be crystallized. To isolate IDA acid from the dilute solution, the processing equipment which is needed includes an evaporator, a cooling crystallizer, centrifuge, solids handling equipment, and storage bin or silo. To control the concentration of impurities which accumulate during recycle of liquor, a small purge stream must be removed.

Another route to PMIDA is from the alkali metal salt of IDA, which, due to limited solubility of co-product alkali metal chloride, leads to very large quantities of effluent, excessively large processing equipment and lower than optimal recovery of PMIDA. Such a process is described in U.S. Pat. Nos. 4,724,103 and 4,775,498. PMIDA crystals are isolated. The mother liquor contains the by-products generated during the reaction and the excess unreacted $H_3PO_3$ and formaldehyde, plus all the sodium from the disodium iminodiacetate used, in the form of sodium chloride. This liquor is not a practical recycle stream without evaporation of a large quantity of water to precipitate the NaCl, and is therefore a waste stream. In addition, $PCl_3$ is conventionally added to a hot alkaline aqueous salt solution of IDA, which results in a violently exothermic reaction that is dangerous and must be carried out in an anaerobic system due to the generation of spontaneously flammable by-products. A build-up of elemental phosphorous in the $PCl_3$ addition pipe also occurs.

It is therefore an object of the present invention to provide a process for preparing phosphonomethyliminodiacetic acid that eliminates the drawbacks of the prior art processes.

It is a more specific object of the present invention to provide a process for preparing phosphonomethyliminodiacetic acid that minimizes the generation of effluent.

It is yet a further object of the present invention to provide a process for preparing phosphonomethyliminodiacetic acid that maximizes the utilization of valuable raw materials.

SUMMARY OF THE INVENTION

The problems of the prior art have been overcome by the present invention, which provides a process for the preparation of phosphonomethyliminodiacetic acid and phosphonomethylglycine in high yields. In general terms, the present invention provides an improved process for the preparation of PMIDA wherein an alkali metal salt of IDA, such as disodium IDA, is reacted with a strong mineral acid ($pK_a$ less than that of phosphorous acid), such as HCl, to convert the salt of IDA to substantially IDA. The IDA is then converted to its highly soluble IDA phosphite salt by the addition of phosphorous acid, and the alkali metal salt (for example, sodium chloride) of the strong acid formed precipitates and can be removed. On the other hand, if excess HCl is added, IDA hydrochloride precipitates, along with the alkali metal chloride, because of its limited solubility under similar conditions. The phosphite salt of IDA obtained can be phosphonomethylated without further recovery or purification, such as by the addition of $PCl_3$ and formaldehyde. Solid PMIDA is then isolated from this matrix and the mother liquor and is preferably recycled. Oxidation of the PMIDA obtained leads to glyphosate.

DETAILED DESCRIPTION OF THE INVENTION

Preferably, the alkali metal salt of IDA used as a starting reactant in the process of the present invention is disodium IDA, although other metal salts thereof, in particular, alkali metal salts such as $M_xH_{(2-x)}$ IDA (where M is an alkali metal and x is from greater than 0 to 2), including but not limited to dipotassium IDA, also may be used. For purposes of brevity, the following description will refer to the alkali metal salt of IDA as the starting material, although those skilled in the art will appreciate that the following is applicable to other metal salts of IDA as well.

The concentration of the alkali metal IDA used in the instant process should be about 10–50% by weight as IDA, preferably about 30–45% by weight as IDA. The alkali metal IDA typically includes about 1% free alkali metal hydroxide present as a result of the formation of the salt of IDA via the hydrolysis of iminodiacetonitrile (IDAN). The alkali metal salt of IDA may also be prepared from the oxidation or the oxidative dehydrogenation of diethanolamine in the presence of alkali metal hydroxide.

The alkali metal IDA salt is reacted with a sufficient amount of a strong mineral acid, preferably a stoichiometric amount thereof such as HCl, more preferably a stoichiometric amount of 31% aqueous solution of HCl, to form IDA and the alkali metal salt of the strong acid (e.g., NaCl). A suitable quantity of phosphorous acid is then added, to solubilize the IDA in the form the phosphite salt. The solution may then be concentrated by evaporation to precipitate the alkali metal salt of the strong acid.

In a preferred embodiment of the present invention, the previously discussed HCl and phosphorous acid addition steps are replaced by the addition of phosphorous trichloride ($PCl_3$), which can be hydrolyzed to $HCl/H_3PO_3$ in a portion of neutralized recycle liquor from a previous batch. So hydrolyzing the $PCl_3$ is less violent than were the $PCl_3$ hydrolyzed by direct addition to the alkali metal IDA. The amount of $PCl_3$ is chosen so that the mole ratio of $PCl_3$ to IDA alkali metal salt (e.g., disodium IDA) results in the conversion of nearly all of the alkali metal in the alkali metal IDA to the alkali metal salt (e.g., NaCl). Depending upon the concentration of alkali metal IDA, the slurry can be warmed, if necessary, to keep the IDA in solution as the phosphite salt. The precipitated alkali metal salt of the strong acid is separated by methods known to those skilled in the art, and the cake is washed, such as with water or aqueous alkali metal chloride solution, to displace the IDA phosphite solution. This washing can be conducted with water or recycled liquor as known to those skilled in the art.

A second portion of $PCl_3$ (total charge greater than or equal to 1 eq./eq. alkali metal IDA) can be hydrolyzed in a second portion of acidic recycle liquor. To this is added a portion or all of the IDA phosphite salt solution, and the temperature is raised to over 100° C. Alternatively, the foregoing can be conducted in two steps by adding HCl and phosphorous acid.

The IDA/HCl/phosphorous acid solution is then phosphonomethylated by adding sufficient formaldehyde, i.e., greater than or equal to 1 equivalent per total equivalents of alkali metal IDA, from a formaldehyde source such as formalin, paraformaldehyde, trioxane, etc. to the mixture. The phosphono-methylation temperature generally ranges from about 108°–130° C. The remaining IDA phosphite, if any, can then be added concurrently with the formaldehyde or at a time found to give optimal conversion to PMIDA, such as when an equivalent of formaldehyde to contained IDA has been added to the reactor.

Once all of the formaldehyde has been added, the reaction is maintained at temperature long enough to effect conversion of remaining IDA to PMIDA, generally about 5 minutes to about 2 hours. Surprisingly, the PMIDA spontaneously precipitates without the addition of ethanol or HCl as required with conventional processes.

Due to the large portion of alkali metal chloride that has been removed before the phosphonomethylation reaction, no dilution and/or neutralization is required before isolation of PMIDA. The PMIDA is separated by methods well known to those skilled in the art, and the liquor is optionally reserved for the next batch. The PMIDA can be washed with water to remove contained reaction liquor, and dried.

The resulting PMIDA can be oxidized by conventional means well known to those skilled in the art to produce glyphosate. A suitable method includes those disclosed in co-pending U.S. Ser. No. 08/453,003 and U.S. Pat. No. 3,969,398, the disclosures of which are hereby incorporated by reference.

The instant invention will be better understood by reference to the following specific but non-limiting examples. It is understood that said invention is not limited by these procedures which are offered merely as illustrations; modifications can be made without departing from the spirit and scope of the invention.

EXAMPLE 1

An aqueous synthetic recycle liquor was prepared with the following composition from the appropriate compounds:

| | |
|---|---|
| N-methyliminodiacetic acid | 3.0% |
| iminodiacetic acid (IDA) | 0.5% |
| formaldehyde | 1.3% |
| hydroxymethylphosphonic acid | 1.8% |
| phosphorous acid | 4.0% |
| phosphonomethyliminodiacetic acid | 2.0% |
| hydrochloric acid | 7.7% |
| sodium chloride | 11.1% |

Except for sodium chloride, the composition is typical of PMIDA recycled liquor resulting from the IDA route. IDA, 50% aqueous NaOH, 70% aqueous $H_3PO_3$ and 37% aqueous HCl were used to simulate the use of $PCl_3$, 50% NaOH, and DSIDA containing 10 mole percent free NaOH.

Synthetic liquor (868.1 g), 50% NaOH (186.7 g), and 70% $H_3PO_3$ (410 g) were mixed with cooling. To this solution was added IDA (665.5 g) and 21.2 g NaCl. At about 70° C., everything was in solution. This solution simulated that which would be recovered from the reaction of the synthetic liquor, $PCl_3$ (3.50 moles), NaOH (2.3 moles), DSIDA (5.00 moles) followed by evaporating water (30–35 moles) and removing the precipitated NaCl (approximately 10 moles) by filtration followed by washing the NaCl with water (approximately 5 moles).

A second portion of synthetic liquor (1736 g) was mixed with 37% HCl (591.9 g) and 70% $H_3PO_3$ (234.3 g). This mixture simulates the hydrolysis of $PCl_3$ (2.00 moles) in the liquor containing excess water (695 g).

The first and second portions were combined in a reactor and heated to the boil. Distillate (695 g) was collected and then the condenser was switched to reflux. Formaldehyde, as a 44% aqueous solution, (426.1 g) was pumped into the boiling solution (temperature approximately 112° C.) over 150 minutes. At the end of the formaldehyde addition, the boiling point had dropped to approximately 109° C.

The reaction mass was boiled for an additional 90 minutes, during which time PMIDA began to spontaneously precipitate from solution. The reaction mass was then cooled to 40° C. and held with stirring overnight.

In the morning the PMIDA was recovered by filtration. The cake was washed with aliquots of water until the liquor ran colorless. The dried cake weighed 1086 g and analyzed by copper chelometric titration to be 99.6% pure. This calculates to a recovery of 95.3%.

EXAMPLE 2

Liquor from Example 1 (868 g) was mixed with 50% aqueous NaOH (146.7 g) then $PCl_3$ (481 g) was added while keeping the temperature below 55° C. After all of the $PCl_3$ had hydrolyzed, 45% aqueous DSIDA solution (1967 g) containing 10 mole percent free NaOH was added. This solution was heated to the boil and 902 g of water was removed by distillation. The IDA phosphite salt solution obtained was filtered to remove the precipitated NaCl and the filter cake was washed twice with 150 ml portions of water. The NaCl recovered weighed 433 g after drying versus the theoretical weight of approximately 590 g.

$PCl_3$ was added to liquor from Example 1 (1736 g) while keeping the temperature $\leq$35° C. This $HCl/H_3PO_3$ solution was combined with the IDA phosphite salt solution filtrate obtained above and heated to the boil.

Forty-four percent aqueous formaldehyde solution (426 g) was added over 150 minutes followed by a 90 minute reflux period. The slurry was cooled to 40° C. and held overnight with stirring.

The PMIDA that formed was recovered by filtration and the cake was washed with water and dried. Chelometric titration indicated a purity of 93.6% giving a recovery of 953.8 g PMIDA. This calculates to a recovered yield of 84.0%. An additional 103.1 g of PMIDA was found in the liquor.

EXAMPLE 3

A synthetic liquor was made by mixing 139.5 g of 37% HCl, 69 g NaCl, and 391.5 g $H_2O$.

Synthetic liquor (84.8 g), 50% NaOH (16.0 g), 70% $H_3PO_3$ (41.0g), and IDA acid (66.6 g) were mixed and then heated to the boil. Water (15 g) was evaporated, then the mixture was centrifuged to remove the precipitated NaCl. The NaCl wet cake was washed with 12 g of water and after drying weighed 58 g. The IDA phosphite liquor was saved.

A 500 ml glass pressure reactor with stirrer was charged with the synthetic liquor (169.6 g), 37% HCl (59.2 g), and 70% $H_3PO_3$ (23.4 g). The solution was heated to the boil and 55.1 g $H_2O$ evaporated. The IDA phosphite liquor was then added, the reactor sealed, and the reaction mass heated to 125° C. Formaldehyde (44.3 g) was pumped into the reaction mass over 65 minutes and the reaction maintained at 125° C. for 30 minutes more. PMIDA precipitated as soon as the reaction mix started to cool.

The cool reaction mass was filtered to recover the PMIDA which, after drying, weighed 78.0 g and analyzed as 98.7% PMIDA. This is a recovery of 67.8%, but an additional 18.1% was found in the liquor, bringing the total conversion to 85.9%. The liquor contained 4.7 mole % unreacted IDA.

EXAMPLE 4

Liquor from Example 3 (89.8 g), 50% NaOH (14.4 g), 70% $H_3PO_3$ (41.0 g), NaCl (61.4 g) and IDA (66.6 g) were mixed and then heated to the boil. Water (9.1 g) was evaporated, then the mixture was centrifuged to remove the precipitated NaCl. The NaCl wet cake was washed with 5.7 g of water and after drying, weighed 55.3 g. The IDA phosphite liquor was saved.

A 500 ml glass pressure reactor with stirrer was charged with the liquor from Example 3 (179.6 g), 37% HCl (59.2 g), and 70% $H_3PO_3$ (23.4 g). The solution was heated to the boil and 55.1 g of water was evaporated. The IDA phosphite liquor was then added, the reactor sealed, and the reaction mass heated to 125° C. Formaldehyde (44.3 g) was pumped into the reaction mass over 63 minutes and the reaction maintained at 125° C. for 30 minutes more. PMIDA precipitated as soon as the reaction mix started to cool.

The cool reaction mass was filtered to recover PMIDA which, after drying, weighed 97.5 g and analyzed as 92.4% PMIDA. This is a recovery of 79.4%.

IDA conversion to PMIDA based on recovered PMIDA and liquor analyses was 81.5%.

EXAMPLE 5

Liquor from Example 4 (89.8 g), 50% NaOH (15.0 g), 70% $H_3PO_3$ (41.0 g), NaCl (61.4 g), and IDA (66.6 g) were mixed and then heated to the boil. Water (9.1 g) was evaporated, then the mixture was centrifuged to remove the precipitated NaCl. The NaCl wet cake was washed with 5.7 g of water and after drying, weighed 57.1 g. The IDA phosphite liquor was saved.

A 500 ml glass pressure reactor with stirrer was charged with the liquor from Example 4 (179.6 g), 37% HCl (59.2 g), and 70% $H_3PO_3$ (23.4 g). The solution was heated to the boil and 55.1 g of water was evaporated. Eighty percent of the IDA phosphite liquor was then added, the reactor sealed, and the reaction mass heated to 125° C. Formaldehyde (22.2 g) was pumped into the reaction mass over approximately 30 minutes and the remaining IDA solution was then added over 4 minutes. The remaining formaldehyde (22.1 g) was added over approximately 30 minutes and the reaction maintained at 125° C. for 30 minutes more. PMIDA precipitated as soon as the reaction mix started to cool.

The cool reaction mass was filtered to recover PMIDA which, after drying, weighed 83.5 g and analyzed as 99.7% PMIDA. This is a recovery of 73.4%. IDA conversion to PMIDA based on recovered PMIDA and liquor analyses was 76.7%.

EXAMPLE 6

Liquor from Example 5 (88.4 g), 50% NaOH (16.0 g), 70% $H_3PO_3$ (41.0 g), NaCl (3.5 g), and IDA acid (66.6 g) were mixed and then heated to approximately 80° C. to dissolve the IDA (the NaCl charge was reduced to eliminate the isolation step, thus simplifying the laboratory work).

A 500 ml glass pressure reactor with stirrer was charged with the liquor from Example 5 (176.7 g), 37% HCl (59.2 g), and 70% $H_3PO_3$ (23.4 g). The solution was heated to the boil and 68.1 g of water was evaporated. The IDA phosphite liquor was then added, the reactor sealed, and the reaction mass heated to 125° C. Formaldehyde (44.3 g) was pumped into the reaction mass over 48 minutes and the reaction maintained at 125° C. for 30 minutes more. PMIDA precipitated as soon as the reaction mix started to cool.

The cool reaction mass was filtered to recover PMIDA which, after drying, weighed 107.6 g and analyzed as 98.7% PMIDA. This is a recovery of 93.5%. IDA conversion to PMIDA based on recovered PMIDA and starting and finished liquor analysis was 87.1%.

EXAMPLE 7

Liquor from Example 6 (88.4 g), 50% NaOH (16.0 g), 70% $H_3PO_3$ (41.0 g), NaCl (3.5 g), and IDA (66.6 g) were mixed and then heated to approximately 80° C. to dissolve the IDA (the NaCl charge was reduced to eliminate the isolation step, thus simplifying the laboratory work).

A 500 ml glass pressure reactor with stirrer was charged with the liquor from Example 6 (176.7 g), 37% HCl (59.2 g), and 70% $H_3PO_3$ (23.4 g). The solution was heated to the boil and 68.1 g of water was evaporated. The IDA phosphite liquor was then added, the reactor sealed, and the reaction mass heated to 125° C. Formaldehyde (44.3 g) was pumped into the reaction mass over 52 minutes and the reaction maintained at 125° C. for 30 minutes more. PMIDA precipitated as soon as the reaction mix started to cool.

The cool reaction mass was filtered to recover PMIDA which, after drying, weighed 93.5 g and analyzed as 99.8% PMIDA. This is a recovery of 82.3%. No unreacted IDA was found in the mother liquor. IDA conversion to PMIDA based on recovered PMIDA and liquor analyses was 84.2%.

EXAMPLE 8

Liquor from Example 7 (88.4 g), 50% NaOH (16.0 g), 70% $H_3PO_3$ (41.0 g), NaCl (3.5 g), and IDA acid (66.6 g) were mixed and then heated to approximately 80° C. to dissolve the IDA acid (the NaCl charge was reduced to eliminate the isolation step, thus simplifying the laboratory work).

A 500 ml glass pressure reactor with stirrer was charged with the liquor from Example 7 (176.7 g), 37% HCl (59.2 g), and 70% $H_3PO_3$ (23.4 g). The solution was heated to the boil and 68.1 g of water was evaporated. The IDA phosphite liquor was then added, the reactor sealed, and the reaction mass heated to 125° C. Formaldehyde (44.3 g) was pumped into the reaction mass over 72 minutes and the reaction maintained at 125° C. for 30 minutes more. PMIDA precipitated as soon as the reaction mix started to cool.

The cool reaction mass was filtered to recover PMIDA which, after drying, weighed 100.6 g and analyzed as 100.2% PMIDA. This is a recovery of 88.6%. No unreacted IDA was found in the mother liquor. IDA conversion to PMIDA based on recovered PMIDA and liquor analyses was 94.2%.

EXAMPLE 9

Liquor from Example 8 (88.4 g), 50% NaOH (16.0 g), 70% $H_3PO_3$ (41.0 g), NaCl (3.5 g), and IDA (66.6 g) were mixed and then heated to approximately 80° C. to dissolve the IDA acid (the NaCl charge was reduced to eliminate the isolation step, thus simplifying the laboratory work).

A 500 ml glass pressure reactor with stirrer was charged with the liquor from Example 8 (176.7 g), 37% HCl (59.2 g), and 70% $H_3PO_3$ (23.4 g). The solution was heated to the boil and 68.1 g of water was evaporated. The IDA phosphite liquor was then added, the reactor sealed, and the reaction mass heated to 125° C. Formaldehyde (44.3 g) was pumped into the reaction mass over 55 minutes and the reaction maintained at 125° C. for 35 minutes more. PMIDA precipitated as soon as the reaction mix started to cool.

The cool reaction mass was filtered to recover PMIDA which, after drying, weighed 96.2 g and analyzed as 99.6% PMIDA. This is a recovery of 84.4%. IDA conversion to PMIDA based on recovered PMIDA and liquor analyses was 89.8%.

EXAMPLE 10

Liquor from Example 9 (87.5 g), 50% NaOH (16.0 g), 70% $H_3PO_3$ (41.0 g), NaCl (3.5 g), and IDA (66.6 g) were mixed and then heated to approximately 80° C. to dissolve the IDA acid (the NaCl charge was reduced to eliminate the isolation step, thus simplifying the laboratory work).

A 500 ml glass pressure reactor with stirrer was charged with the liquor from Example 9 (175.0 g), 37% HCl (59.2 g), and 70% $H_3PO_3$ (23.4 g). The solution was heated to the boil and 67.3 g of water was evaporated. The IDA phosphite liquor was then added, the reactor sealed, and the reaction mass heated to 125° C. Formaldehyde (42.6 g) was pumped into the reaction mass over 112 minutes and the reaction maintained at 125° C. for 15 minutes more. PMIDA precipitated as soon as the reaction mix started to cool.

The cool reaction mass was filtered to recover PMIDA which, after drying, weighed 108.0 g and analyzed as 100.3% PMIDA. This is a recovery of 95.1%. No unreacted IDA could be found in the mother liquor. IDA conversion to PMIDA based on recovered PMIDA and liquor analyses was 93.4%.

EXAMPLE 11

Liquor from Example 10 (87.5 g), 50% NaOH (16.0 g), 70% $H_3PO_3$ (41.0 g), NaCl (3.5 g), and IDA (66.6 g) were mixed and then heated to approximately 80° C. to dissolve the IDA acid (the NaCl charge was reduced to eliminate the isolation step, thus simplifying the laboratory work).

A 500 ml glass pressure reactor with stirrer was charged with the liquor from Example 10 (175.0 g), 37% HCl (59.2 g), and 70% $H_3PO_3$ (23.4 g). The solution was heated to the boil and 67.3 g of water was evaporated. The IDA phosphite liquor was then added, the reactor sealed, and the reaction mass heated to 125° C. Formaldehyde (44.3 g) was pumped into the reaction mass over 28 minutes and the reaction maintained at 125° C. for 60 minutes more. PMIDA spontaneously precipitated near the end of the hold period.

The cool reaction mass was filtered to recover PMIDA which, after drying, weighed 92.4 g and analyzed as 98.7% PMIDA. This is a recovery of 80.3%. No unreacted IDA could be found in the mother liquor. IDA conversion to PMIDA based on recovered PMIDA and liquor analyses was 94.0%.

EXAMPLE 12

Liquor from Example 11 (87.5 g), 50% NaOH (16.0 g), 70% $H_3PO_3$ (41.0 g), NaCl (3.5 g), and IDA (66.6 g) were mixed and then heated to approximately 80° C. to dissolve the IDA acid (the NaCl charge was reduced to eliminate the isolation step, thus simplifying the laboratory work).

A 500 ml glass pressure reactor with stirrer was charged with the liquor from Example 11 (175.0 g), 37% HCl (59.2 g), and 70% $H_3PO_3$ (23.4 g). The solution was heated to the boil and 67.3 g of water was evaporated. The IDA phosphite liquor was then added, the reactor sealed, and the reaction mass heated to 125° C. Formaldehyde (44.3 g) was pumped into the reaction mass over 55 minutes and the reaction maintained at 125° C. for 45 minutes more. The cool reaction mass was filtered to recover PMIDA which, after drying, weighed 110.6 g and analyzed as 94.5% PMIDA. This is a recovery of 92.0%. No unreacted IDA could be found in the mother liquor.

What is claimed is:

1. A process for producing phosphonomethyliminodiacetic acid, comprising:

a) reacting an aqueous solution containing a metal salt of iminodiacetic acid with a sufficient amount of a strong mineral acid to convert said salt to iminodiacetic acid and the metal salt of said strong acid;

b) adding a phosphorous acid source to the reaction product of step a) to form a solution of iminodiacetic acid phosphite salt;

c) separating the precipitated metal salt of said strong mineral acid from said solution of iminodiacetic acid phosphite salt;

d) phosphonomethylating said iminodiacetic acid phosphite salt with a phosphorous acid source and a formaldehyde source in the presence of a strong mineral acid to produce phosphonomethyl-iminodiacetic acid and a mother liquor; and e) recovering phosphonomethyliminodiacetic acid from said mother liquor.

2. The process of claim 1, further comprising hydrolyzing phosphorous trichloride to form phosphorous acid, and wherein said phosphonomethylating step is performed using said phosphorous acid.

3. The process of claim 1, further comprising oxidizing said phosphonomethyliminodiacetic acid.

4. The process of claim 1, wherein said mother liquor is recycled to a subsequent batch.

5. The process of claim 1, wherein said phosphorous source is $PCl_3$.

6. The process of claim 1, wherein said metal salt of iminodiacetic acid is $M_xH_{(2-x)}$ IDA, where M is an alkali metal and x is from greater than 0 to 2.

7. The process of claim 6, wherein M is sodium and x is 2.

8. The process of claim 1, wherein said sufficient amount of a strong mineral acid is a stoichiometric amount.

9. The process of claim 2, wherein said mother liquor is recycled to a subsequent batch to hydrolyze said phosphorous trichloride.

* * * * *